United States Patent [19]

Valtchev

[11] Patent Number: 5,445,643
[45] Date of Patent: Aug. 29, 1995

[54] CONNECTION MECHANISMS FOR UTERINE MOBILIZER

[76] Inventor: Konstantin L. Valtchev, 43 Cosmic Drive, Don Mills, Toronto, Ontario, Canada, M3B 3G1

[21] Appl. No.: 321,062

[22] Filed: Oct. 7, 1994

Related U.S. Application Data

[63] Continuation of Ser. No. 31,375, Mar. 9, 1993, abandoned.

[51] Int. Cl.⁶ .............. A61B 17/42; A61M 29/00
[52] U.S. Cl. ............................ 606/119; 606/191; 600/220
[58] Field of Search ............... 606/1, 119, 190–198, 606/205, 209; 604/164, 264, 54, 55, 104–106; 128/20, 3, 17

[56] References Cited

U.S. PATENT DOCUMENTS

| | | | |
|---|---|---|---|
| 4,752,292 | 6/1988 | Lopez et al. | 604/905 |
| 4,969,879 | 11/1990 | Lichte | 604/283 |
| 5,047,021 | 9/1991 | Utterberg | 604/905 |
| 5,237,985 | 8/1993 | Hodgson et al. | 128/70 |
| 5,250,038 | 10/1993 | Meller et al. | 604/283 |
| 5,282,800 | 2/1994 | Fosher et al. | 606/205 |
| 5,286,255 | 2/1994 | Weber | 606/205 |

FOREIGN PATENT DOCUMENTS

| | | |
|---|---|---|
| 0169704 | 1/1986 | European Pat. Off. . |
| 0400458 | 3/1991 | European Pat. Off. . |
| 1084427 | 6/1960 | Germany . |

*Primary Examiner*—Stephen C. Pellegrino
*Assistant Examiner*—Glenn Dawson
*Attorney, Agent, or Firm*—Henderson & Sturm

[57] ABSTRACT

A gynecologic instrument or uterine mobilizer having a tube with one end fitted to a tube holder and another end attached to a journal pivotally mounted and maintained within a channel in the head of the instrument via a pin engaging a groove in the head. It is adapted to be disassembled by first releasing the tube from the tube holder and rotating the journal to which the tube is attached a prescribed degree to permit the pin to disengage the groove in the head to permit the tube to be removed from the head.

8 Claims, 7 Drawing Sheets

CONNECTION MECHANISMS FOR UTERINE MOBILIZER

This is a continuation of application Ser. No. 08/031,375 filed on Mar. 9, 1993, now abandoned.

TECHNICAL FIELD

The present invention relates to a gynecologic instrument useful in gynecologic laparoscopy. More particularly, the present invention is directed to a uterine mobilizer or manipulator. Specifically the present invention is directed to an improved uterine mobilizer provided with improved connection mechanism for connecting and disconnecting the head of the instrument to the tube of the instrument.

BACKGROUND ART

In my U.S. Pat. 4,022,208, the disclosure of which in its entirety is incorporated by reference herein, I disclose and claim a gynecologic instrument capable of rotating the uterus to any of its natural positions within the peritoneal cavity which instrument lessens the danger of damage to vaginal and uterine tissue and which instrument may be adopted for injection of dye into a uterus while the uterus is maintained in any of its natural positions.

SUMMARY OF THE INVENTION

The present invention is directed to an improvement to be embodied in gynelogic instruments that is particularly useful when embodied in the gynecologic instrument disclosed and claimed in U.S. Pat. No. 4,022,208.

In the apparatus of the present invention, the improvements reside in means for connecting the tube to the head wherein the tube is fitted or otherwise attached to an end of a piston held in place in the head by a pin which is capable of moving within a groove within the head in such a manner that does not permit removal of the piston from the head as long as the tube is not pivoted about the piston beyond a predetermined degree.

BRIEF DESCRIPTION OF THE DRAWINGS

The invention will be clearly understood after reference to the following detailed specification read in conjunction with the drawings.

In the drawings.

DISCLOSURE OF THE INVENTION

The instrument illustrated in the Figures has a stem, tubing, or tube 1 and a block or head 2 pivotally mounted on the tube by piston 3. The improvements of the present invention are directed to an improved assembly of elements of head 2, tube holder 23, tube sleeve 27.

The head 2 of the apparatus of the present invention is provided with a channel 2a for receiving a journal 3 adapted to rotate or pivot about its axis in the channel 2a. The head is also provided with a groove 9a for receiving a pin 9 attached to the journal 3 for engaging the groove 9a to connect the head 2 to the tube. The pin 9 attached to the journal 3 when inserted in the groove 9a in the head 2 are adapted to prevent removal of the journal 3 from the channel 2a in the head 2 when the pin 9 is positioned within the groove. The pin 9 and the groove 9a are disengaged by rotating the tube 1 attached to the journal 3 by a prescribed degree of rotation until the pin becomes free of the groove to permit the journal 3 to which the tube 1 is attached to be pulled out of the head 2.

As shown in the Figures, tube holder 23 is provided at one end with a luer syringe connector 22 which in turn is connected to a syringe 20. At the opposite end of the tube connector 23 there is a cylindrical cavity 25 having an entrance in which an "0" ring 25a is positioned for receiving the distal end of tube 1. The tube holder 23 is provided with a locking mechanism 24 pivotally attached to the tube holder by a pin or other means 26 which permits rotation of the locking mechanism thereabout. The locking mechanism 24, at the end which points towards the sleeve 27, has a tooth 28 which engages the first groove 28a of the sleeve and locks it in place. The locking mechanism is adapted to pivot about axis 26 in a seesaw or reciprocal manner. To this end, a spring or other means for biasing 29 is provided at one end of the locking mechanism 24 which pushes the locking mechanism up and consequently pushes the tooth downward into the groove at the opposite end of the tube holder.

Figure 10:
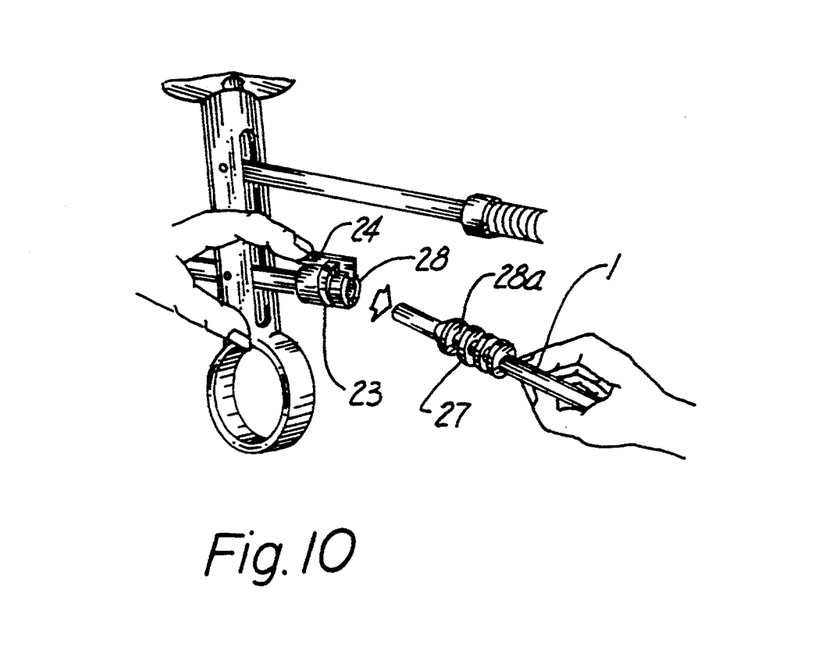
FIG. 10 is an illustration of removing the tube from the tube holder of the apparatus in accordance with the present invention.

As illustrated in FIG. 10, to remove the tube 1 from the tube holder 23, one merely needs to push the end of the locking mechanism 24 over the spring downwardly compressing the spring and lifting the tooth 28 of the locking mechanism up from the groove 28a of the sleeve 27. This releases the sleeve 27 and the tube 1 can be pulled out from the tube holder 23.

As long as the tube 1 is locked into the tube holder 23 during the manipulation of the head 2 from the straight position to a rotation of 120° as shown in FIGS. 2, 4, 5, and 5A, the pin 9 is engaged in the groove 9a of the head 2 and the Journal or piston 3 can not be removed.

The tube 1 can be completely separated from the tube holder 23 and the head 2 in the following way.

Figure 11:
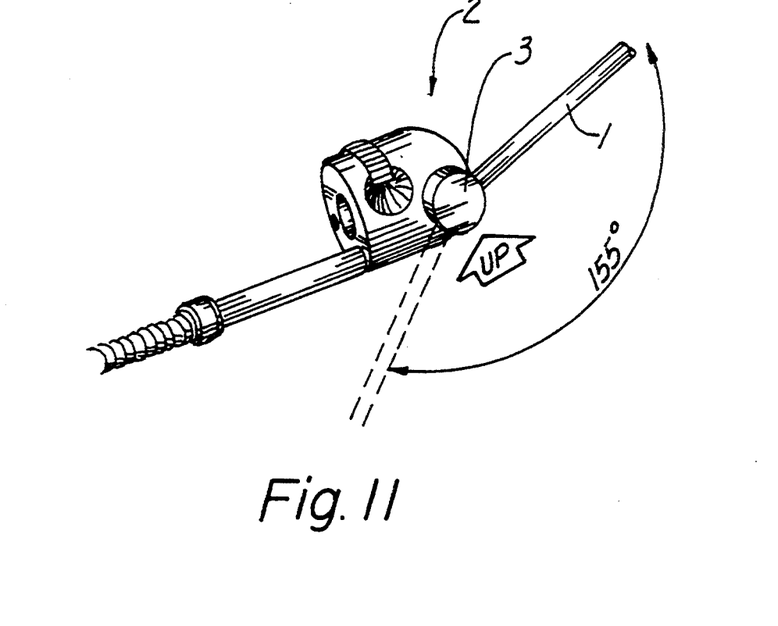
FIG. 11 is an illustration of removing the tube from the head of the apparatus in accordance with the present invention.

The tube 1 is removed from the tube holder 23 as described above; then the tube 1 is rotated counterclockwise as shown in FIG. 11. At that point the pin 9 becomes disengaged from groove 9a, journal piston 3 is in a position to be pulled out from the head 2. To reattach the tube simply follow the removal procedure in reverse order.

In operation all of the elements of the instrument from syringe 20 to hook 7 include passageways, channels or conduits (whether or not clearly shown) to permit the passage of fluid from the syringe, out of the end of hook 7. Thus, fluid may be injected from the syringe 18 into the channel of the extension tube 23a of tube holder 23 and in turn through the channel 1a in tube 1, piston 3a, head 2a, and from there into the cannula 7 which is inserted in cavity 4 and locked into the head.

Head 2 has a substantial flat cervix engaging shoulder that is adapted to abut the vaginal part of the uterus cervix. A recess or cavity 4 is provided in head 2 to receive an obturator, cannula or equivalent device designated generally as hook 7 in U.S. Pat. No. 4,022,208 and shown in FIG. 1 as such. The control link 5 has an extension or spacer bar 6 at its free end. The spacer bar 6 has a through bore 6a so that it can move relative to tube 1. A thumb screw or lock screw 8 threadedly engages in spacer bar 6 and can be turned to tighten against tube 1 to lock the link 5 with respect to tube 1 and fix the angular position of head 2 and hook 7 with respect to tube 1. Thus, the hook 7 can be manipulated to any desired angular position with respect to the tube 1 and maintained in that position by the set thumbscrew 8.

Figure 1:
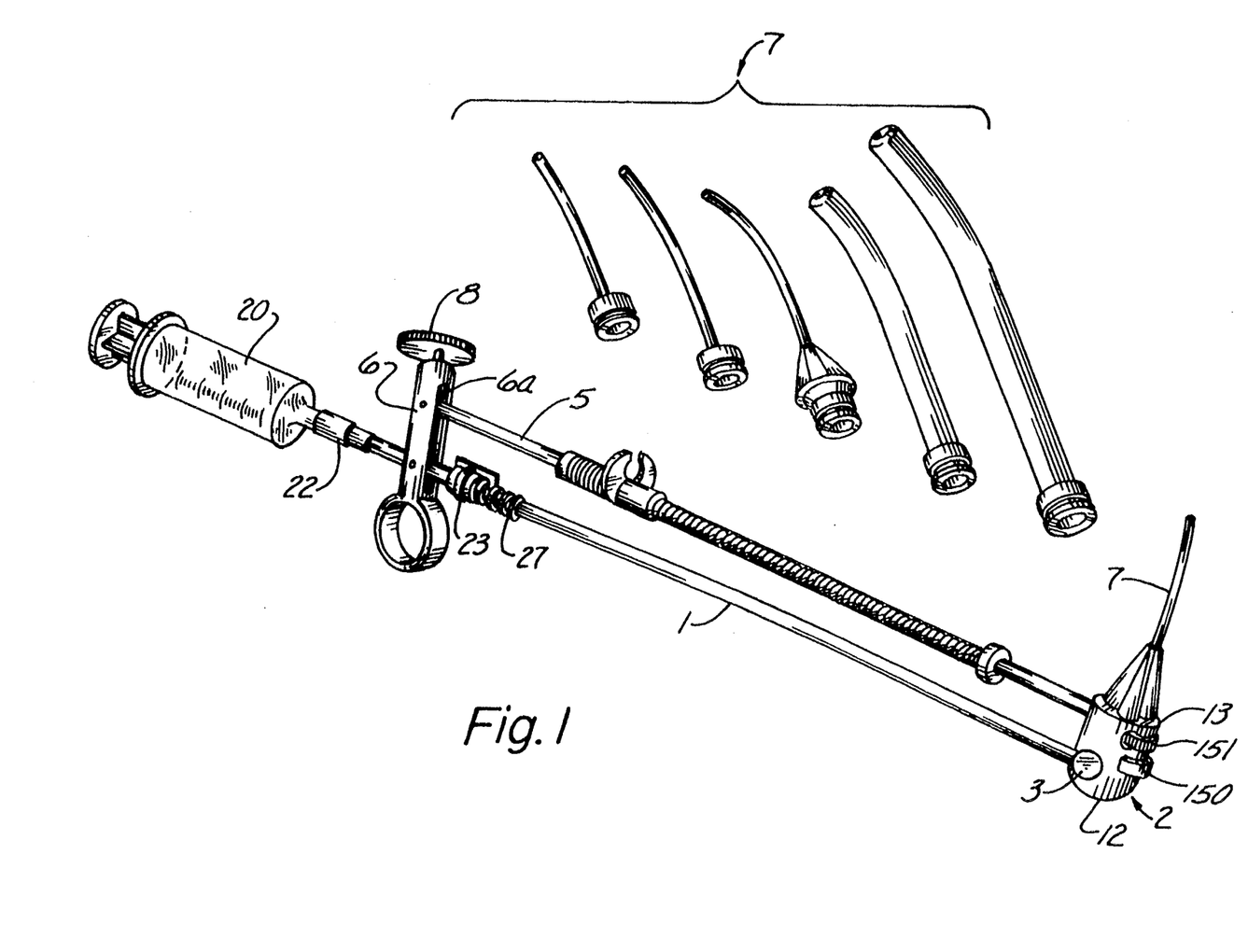
FIG. 1 is a side view elevational of an apparatus in accordance with the present invention.
Figures 2, 3, 4, 5:
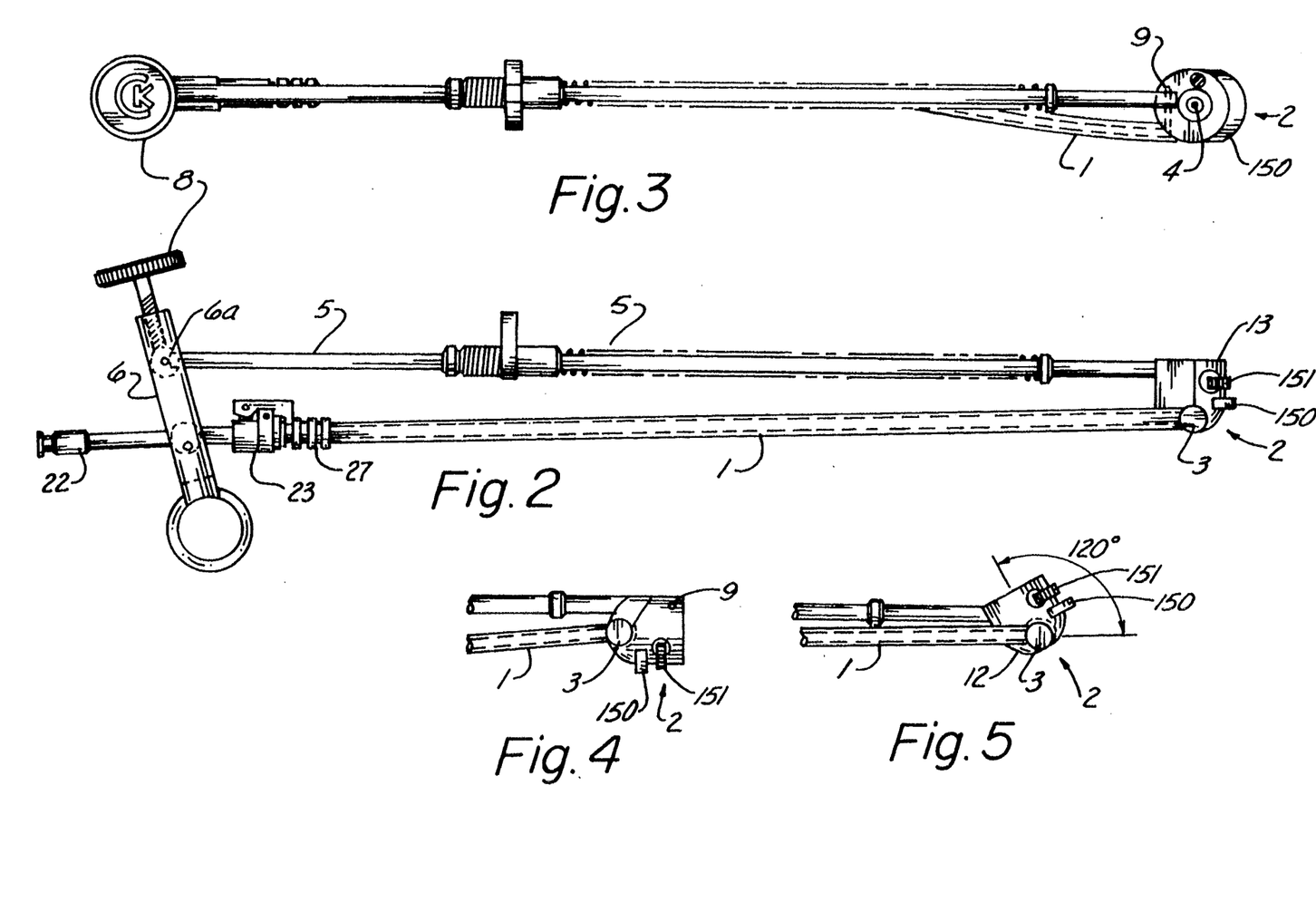
FIG. 2 is a side view of an apparatus in accordance with the present invention.
FIG. 3 is a top view of an apparatus in accordance with the present invention.
FIG. 4 is a partial side view of an apparatus in accordance with the present invention showing the head in the fully extended position.
FIGS. 5 and 5a are partial side views of an apparatus in accordance with the present invention showing the head in the fully flexed position.
Figures 2A, 5A:
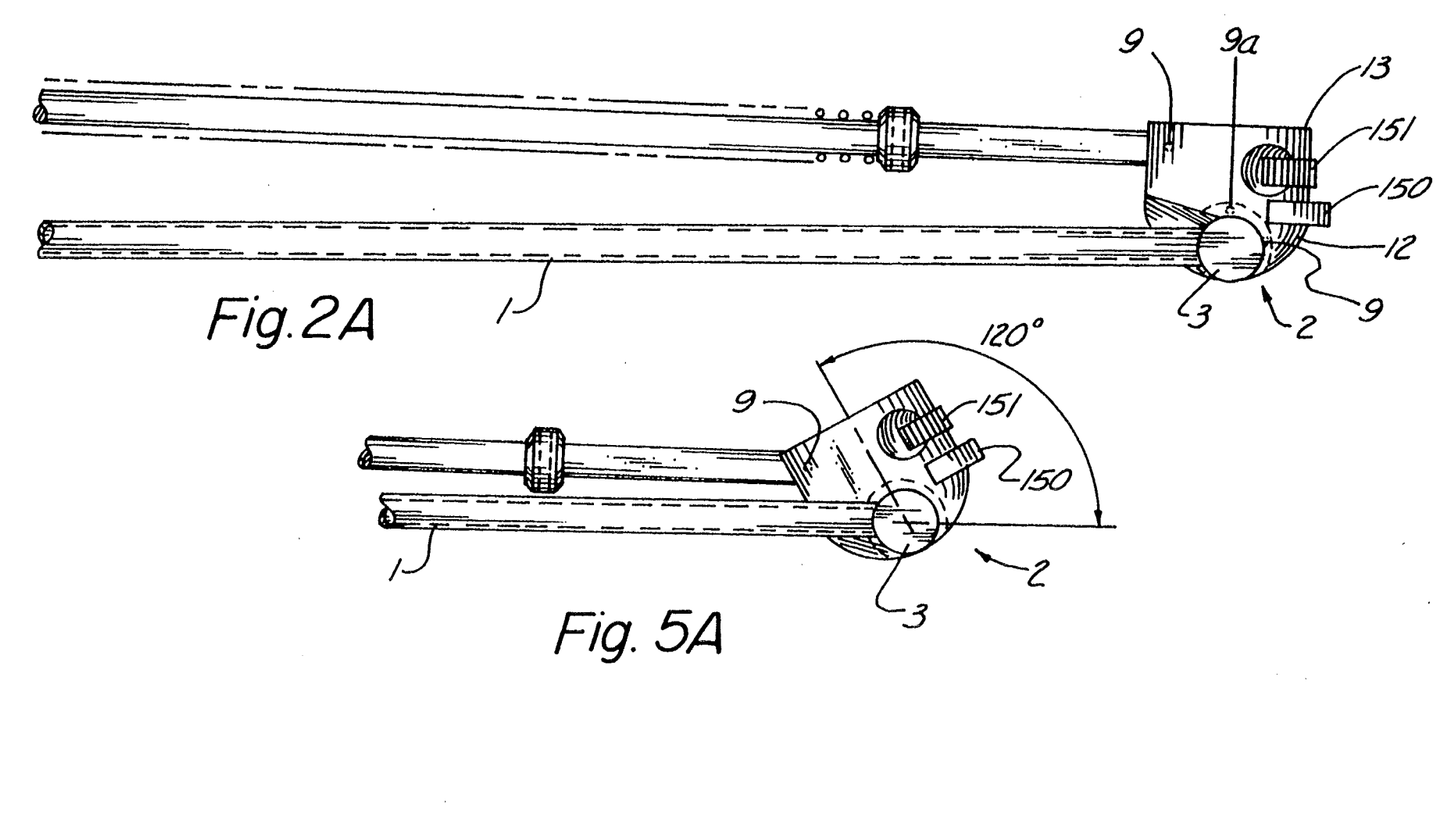
FIG. 2a is a partial side view of the head end of the apparatus in accordance with the present invention.
Figure 6:
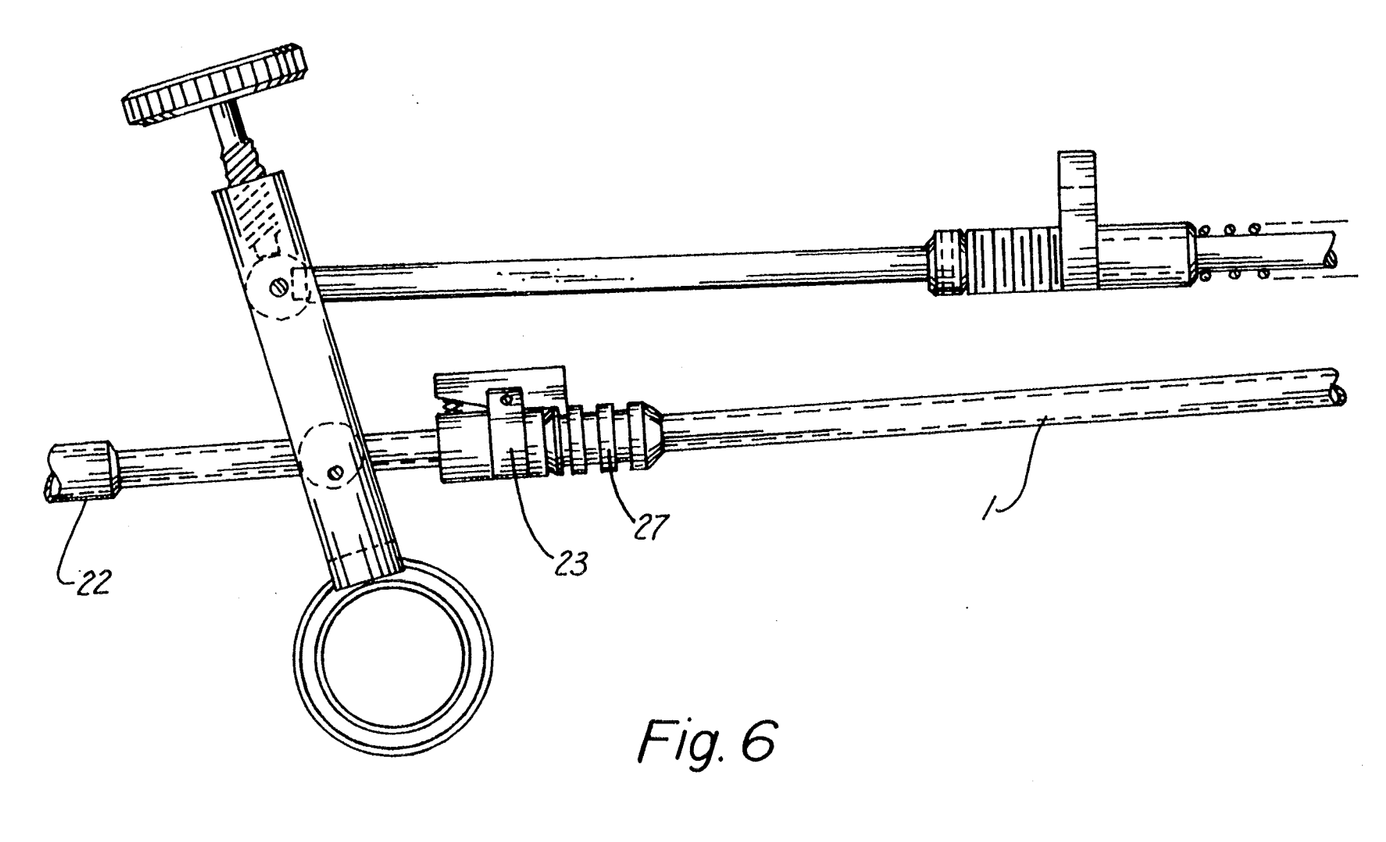
FIG. 6 is a partial side view of the tail end of the apparatus in accordance with the present invention.
Figure 7:
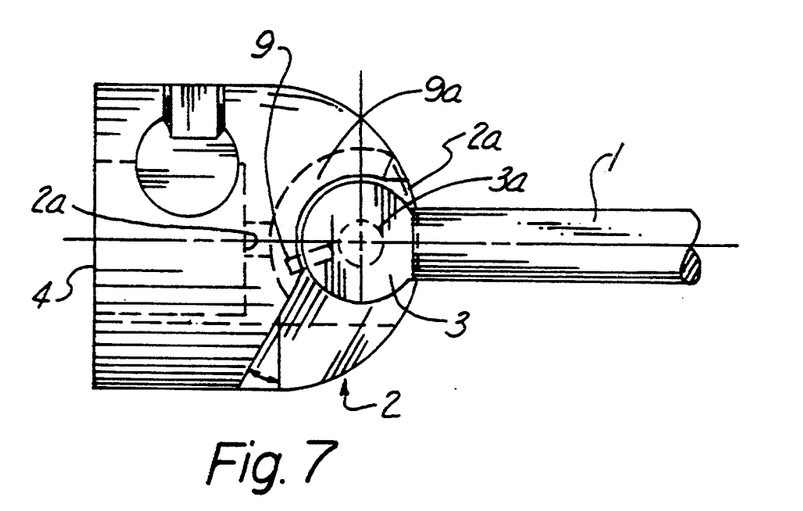
FIG. 7 is a cross-sectional view of the head of the apparatus of the present invention.
Figure 8:
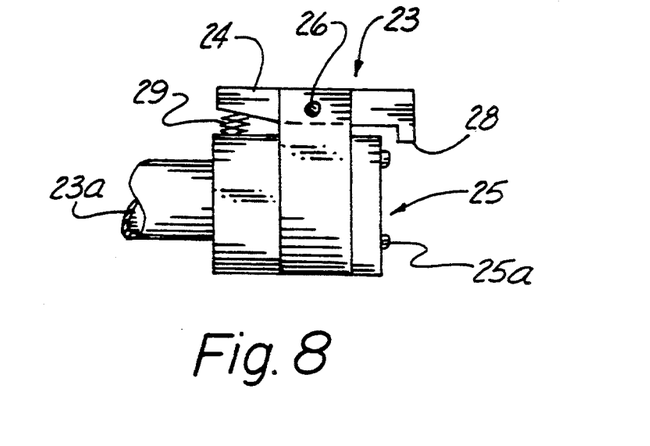
FIG. 8 is a cross-sectional view of the tube holder of the apparatus of the present invention.
Figure 9:
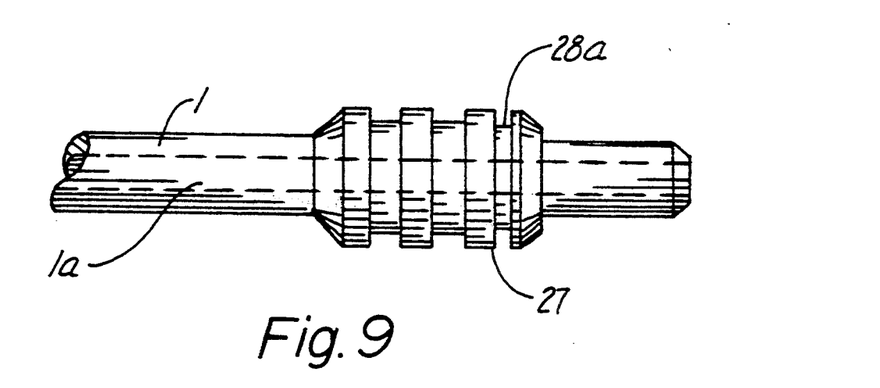
FIG. 9 is a cross-sectional view of the sleeve on the tube for connection with the tube holder of the apparatus of the present invention.

Head 2 includes a substantially part spherical surface 12 opposite shoulder 13. This surface must be smooth in order to minimize the chances of injury to sensitive vaginal tissue during rotation of head 2 about journal or piston 3. A partial spherical surface is the most desirable shape although other smooth contours may be employed. As the uterus is moved by the movement of cannula 7, ligaments attached to the uterus may cause the instrument to be pressed against the vaginal wall. Thus, the smooth part spherical surface will distribute any such pressure and support the instrument and uterus throughout the full range of possible positions. Shoulder 13 ensures that excess penetration of cannula 7 will not occur during movement of the uterus. A range of sizes of cannula obturator or similar devices 7, as shown in FIG. 1, may be provided to accommodate any particular patient or condition. A properly chosen size of the cannula or equivalent device and the action of shoulder 13 will together eliminate the danger of perforating the uterus during use of the instrument.

A control link 5 pivotally connects the proximal end thereof with the head 2 by pin 9 and extends from its pivotal connection therewith to adjacent the free distal end of the tube 1. Tube 1 may be provided with a grip (not shown) at the distal end thereof. Preferably such a grip can include a syringe 20. The free distal end of tube 1 may also be provided with a grip, such as the one identified as element 2 in the U.S. Pat. No. 4,022,208. In either case, a surgeon can, by moving the grips or the distal ends of the spacer bar 5 and tube 1 away from or towards each other in the directions of the arrows 22, rotate head about its pivotal connection with the tube. Thus, a cannula or equivalent device 7 can be caused to move from one dotted line position shown in FIGS. 12, and 13, though the solid line position to the other dotted line position whereby to move the cannula to any desired angular position with respect to the tube. While a greater arc of rotation may be provided the instrument will usefully serve its intended function if the head is pivoted so as to permit movement of the cannula through an arc of at least approximately 135°. To achieve full natural rotation of the uterus, link 5 must be capable of pivoting the cannula from a position where the tube and cannula are substantially parallel to a position where the angle between the tube and the cannula is not greater than about 45°. This is described in more detail in U.S. Pat. No. 4,022,208.

Figure 12:
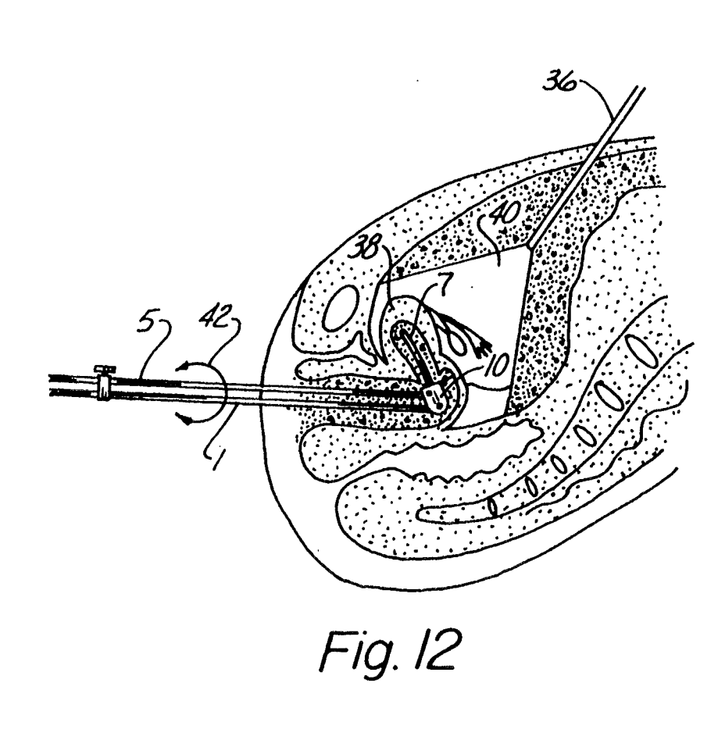
FIGS. 12 and 13 are schematic illustrations of the general manner of use of the apparatus in accordance with the present invention.
Figure 13:
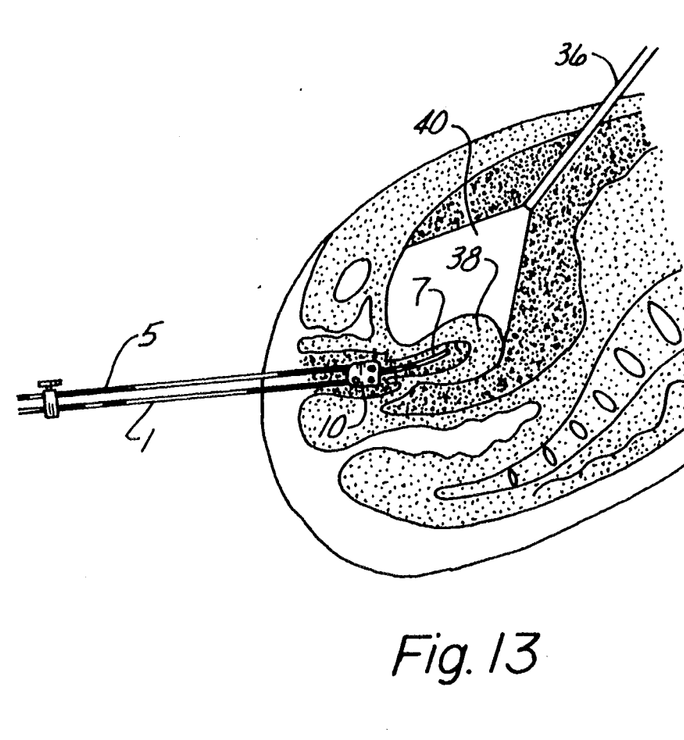

FIGS. 12 and 13 are schematic illustrations of a gynecologic laparoscopy showing the patient in Trendelenburg position, as disclosed in U.S. Pat. No. 4,022,208, and the laparoscope 36 in position to view the uterus 38. The field of vision of the laparoscope is indicated by the numeral 40. The instrument may be used in association with a tenaculum in the conventional manner. Coil spring 15 would on control link 5 and sliding fitting or tenaculum holder 16 for a tenaculum facilitate such use.

The obturator, cannula, or hook 7 of the instrument is inserted into the uterus through the vaginal opening until the cervix engaging shoulder 12 abuts against the cervix of the uterus. Shoulder 12 thus limits the depth of penetration of obturator 7 into the uterus and also supports the uterus as it is moved to the desired position. By manipulation of link 5 and tube 1, e.g. via grips provided at their distal ends; towards or away from each other a surgeon can support the uterus in any position in a vertical or medium sagittal plane from the one illustrated in FIG. 12 to the one illustrated in FIG. 13. This range of vertical positioning gives excellent opportunity for laparoscope inspection. As shown in FIG. 12, the uterus may be flexed to the natural position closest to the abdominal wall. By tightening thumb screw 8 one can fix the obturator 7 in any desired angular position with respect to the tube 1. Thus, the uterus may be maintained at any desired position in the vertical or median sagittal plane. After the uterus has been located in a desired position, the instrument may be rotated about the longitudinal axis of tube 1 in the direction of the arrow 42 shown in FIG. 12. Thus, the uterus may be rotated either to the left or right while close to the abdominal wall giving the surgeon an excellent lateral view.

As disclosed above, the instrument facilitates injection of gases or liquid into the uterus when the obturator 7 is tubular in nature and tube 1 is provided at its distal end with a syringe 20 for providing a gas or liquid through tube 1 which thus functions as a conduit to the head of the obturator 7 as a gas or liquid supply line as disclosed in U.S. Pat. No. 4,022,208.

Related to this, as disclosed in U.S. Pat. No. 4,022,208, a tubular hook 7a may be provided with openings 24 for passage of fluid. The hook 7a may be provided with a tubular extension 15 by means of which a flexible conduit 16 may be fluidly connected to hook 7a. The conduit advantageously passes from the end of such a tubular portion 15 of hook 7a through a fluid passageway in piston 3 through head 2 and thence in a direction parallel to tube 1. Fluid can then be passed through the tube by means of a syringe 18 or other conventional means. Such a modified instrument provides the gynecologist with the ability to inject gases or liquids including dyes while the uterus is maintained in any of its natural positions.

The general method of performing a gynecologic laparoscopy is well known and not referred to in detail.

It is well described in the book, "Laparoscopy, Culdoscopy and Gynecography," by Melvin R. Cohen, published 1970 by W. B. Saunders Company of Philadelphia, Pa. London, Ontario and Toronto, Ontario.

It will be appreciated to those of ordinary skill in the art that, while the present invention has been described herein by reference to particular means, methods, and materials, the scope of the present invention is not limited thereby, and extends to any and all other means, methods, and materials suitable for practice of the present invention.

What is claimed is:

1. A gynecologic instrument comprising:
   a) a tube having a proximal end and a distal end;
   b) a tube holder fitted in a releasable manner to the distal end of said tube;
   c) a journal having an end attached to the proximal end of said tube, said journal comprising a pin; and
   d) a head comprising an opening along a pivotal axis of the head with respect to said tube for receiving said journal and a groove for receiving said pin, said journal being pivotally fitted in said opening and said pin engaging said groove to pivotally connect said tube in a pivotally releasable manner to said head.

2. The gynecologic instrument of claim 1, wherein said distal end of said tube comprises a fitting.

3. The gynecologic instrument of claim 2, wherein said tube holder comprises a means for engaging said fitting.

4. The gynecologic instrument of claim 3, wherein said fitting comprises a recessed area for receiving said means for engaging.

5. The gynecologic instrument of claim 4, wherein said means for engaging comprises a projection adapted to fit in said recessed area of said fitting.

6. The gynecologic instrument of claim 5, wherein said projection is spring-biased to engage said recessed area.

7. The gynecologic instrument of claim 1, wherein said groove and said pin are adapted to be disengaged by rotating said tube about said journal by a prescribed degree of rotation.

8. The gynecologic instrument of claim 1, comprising a passageway through said tube, said journal and said head to permit the passage of fluid therethrough.

* * * * *